United States Patent
Lal et al.

(10) Patent No.: US 7,049,472 B2
(45) Date of Patent: May 23, 2006

(54) BIS(3-ALKOXYALKAN-2-OL) SULFIDES, SULFONES, AND SULFOXIDES: NEW SURFACE ACTIVE AGENTS

(75) Inventors: Gauri Sankar Lal, Whitehall, PA (US); Williams Rene Edouard Raymond, New Tripoli, PA (US); Khalil Yacoub, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/899,419

(22) Filed: Jul. 26, 2004

(65) Prior Publication Data

US 2006/0020144 A1    Jan. 26, 2006

(51) Int. Cl.
*C07C 241/00* (2006.01)
(52) U.S. Cl. .......... 564/463; 564/503; 564/18; 568/504; 568/38; 568/39; 568/41; 568/45; 568/300; 568/579
(58) Field of Classification Search ......... 564/463, 564/503, 18; 568/504, 38, 39, 41, 45, 300, 568/579, 583, 589
See application file for complete search history.

(56) References Cited

U.S. PATENT DOCUMENTS

| | | | |
|---|---|---|---|
| 3,277,163 A | 10/1966 | Waldmann et al. | |
| 3,488,348 A | 1/1970 | Mayer et al. | |
| 3,848,028 A | 11/1974 | Engelhard et al. | |
| 3,988,377 A | 10/1976 | Lamberti et al. | |
| 5,585,517 A | 12/1996 | Deisenroth et al. | |

FOREIGN PATENT DOCUMENTS

| | | |
|---|---|---|
| DE | 1670657 | 12/1970 |
| GB | 1120652 | 7/1968 |
| JP | 09302029 A * | 11/1997 |
| SU | 1268572 A1 | 11/1968 |

OTHER PUBLICATIONS

Brittain, J., et al., Triphenylsilanethiol: A Solid $H_2S$ Equivalent in the Ring Opening of Epoxides, Tetrahedron Letters, vol. 34, No. 21, pp. 3363-3366 (1993).
European Search Report, No. 05015618.1-2108 dated Nov. 30, 2005.

* cited by examiner

*Primary Examiner*—Johann Richter
*Assistant Examiner*—Chukwuma Nwaonicha
(74) *Attorney, Agent, or Firm*—Michael Leach

(57) ABSTRACT

Compositions containing surfactant compounds according to formula (I)

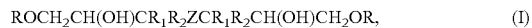

wherein Z is S, SO, or $SO_2$, can have a range of equilibrium and/or dynamic surface tensions and a range of foaming performance attributes, depending upon the particular values of Z, R, $R_1$, and $R_2$. The compounds of formula (I) may be prepared by a process that includes reaction of a sulfide source such as a metal sulfide or bisulfide with an alkyl glycidyl ether.

37 Claims, No Drawings

BIS(3-ALKOXYALKAN-2-OL) SULFIDES, SULFONES, AND SULFOXIDES: NEW SURFACE ACTIVE AGENTS

FIELD OF THE INVENTION

This invention relates to surfactant compositions. More particularly, it relates to adducts of sulfides with glycidyl ethers and their use to reduce the surface tension in water-based systems.

BACKGROUND OF THE INVENTION

The ability to reduce the surface tension of water is of great importance in the application of water-based formulations because decreased surface tension translates to enhanced substrate wetting during use. Examples of water-based compositions requiring good wetting include coatings, inks, adhesives, fountain solutions for lithographic printing, cleaning compositions, metalworking fluids, agricultural formulations, electronics cleaning and semiconductor processing compositions, personal care products, and formulations for textile processing and oilfield applications. Surface tension reduction in water-based systems is generally achieved through the addition of surfactants, resulting in enhanced surface coverage, fewer defects, and more uniform distribution. Equilibrium surface tension (EST) is important when the system is at rest, while dynamic surface tension (DST) provides a measure of the ability of a surfactant to reduce surface tension and provide wetting under high speed application conditions.

The importance of the ability of a surfactant to achieve low surface tension at low use levels, the ability to affect foaming performance, and the surfactant's ability to provide efficient emulsification and solubilization are all of considerable industrial importance, as is well-appreciated in the art. And, although equilibrium surface tension reduction efficiency is important for some applications, other applications may require both equilibrium and dynamic surface tension reduction.

The foaming characteristics of a surfactant are also important because they can help define applications for which the surfactant might be suitable. For example, foam can be desirable for applications such as ore flotation and cleaning. On the other hand, in coatings, graphic arts and adhesive applications, foam is undesirable because it can complicate application and lead to defect formation. Thus foaming characteristics are frequently an important performance parameter.

The wide variety of applications for which surfactants are used, and the resultant variation in performance requirements, results in a need for a correspondingly large number of surfactants adapted to these various performance demands, and a need for suitable methods for making them.

SUMMARY OF THE INVENTION

In one aspect, the invention provides a composition including a compound according to formula (I)

ROCH$_2$CH(OH)CR$_1$R$_2$ZCR$_1$R$_2$CH(OH)CH$_2$OR    (I).

Each R is independently selected from the group consisting of C4–C20 branched, linear, and cyclic alkyl, alkenyl, aryl, and aralkyl moieties; C4–C20 branched, linear, and cyclic alkyl, alkenyl, aryl, and aralkyl moieties bearing a carbonyl group or one or more heteroatoms selected from O, S, and N; glycol ether moieties of the formula R$_3$(OCH$_2$CH$_2$)$_n$—; aminoethylene moieties of the formula R$_3$(NHCH$_2$CH$_2$)$_n$—; and thioether moieties of the formula R$_3$S(CH$_2$)$_n$—. R$_3$ is H or linear C1–C12 alkyl, n is an integer from 1 to 15, R$_1$ and R$_2$ are each independently H or a C1–C4 alkyl group, and Z is S, SO, or SO$_2$.

In another aspect, the invention provides a method of preparing a compound according to formula (I) as shown above, The method includes contacting at least one compound according to formula (II)

with a sulfide source. R is selected from the group consisting of C4–C20 branched, linear, and cyclic alkyl, alkenyl, aryl, and aralkyl moieties; C4–C20 branched, linear, and cyclic alkyl, alkenyl, aryl, and aralkyl moieties bearing a carbonyl group or one or more heteroatoms selected from O, S, and N; glycol ether moieties of the formula R$_3$(OCH$_2$CH$_2$)$_n$—; aminoethylene moieties of the formula R$_3$(NHCH$_2$CH$_2$)$_n$—; and thioether moieties of the formula R$_3$S(CH$_2$)$_n$—. R$_3$ is H or linear C1–C12 alkyl,n is an integer from 1 to 15, R$_1$ and R$_2$ are each independently H or a C1–C4 alkyl group, and Z is S, SO, or SO$_2$.

DETAILED DESCRIPTION OF THE INVENTION

The present invention relates to novel surfactant compositions that are capable of effectively reducing the dynamic and/or equilibrium surface tension of aqueous systems, and/or affecting foaming performance of such systems. The compositions include bis(3-alkoxyalkan-2-ol)-sulfides, sulfones, and sulfoxides according to the following formula (I), wherein Z represents S, SO, or SO$_2$, respectively:

ROCH$_2$CH(OH)CR$_1$R$_2$ZCR$_1$R$_2$CH(OH)CH$_2$OR    (I)

Each R is independently a C4–C20 alkyl, alkenyl, aryl, or aralkyl moiety, and may be branched, linear, or cyclic. It may also be such a moiety bearing a carbonyl group, especially a carboxylic acid, ester, or amide, and/or one or more heteroatoms selected from O, S, and N. Such moieties may be in any location on R. Typically R is a C8–C18 linear alkyl group, and more typically it is a C12–C16 linear alkyl group. R may also be a glycol ether moiety of the formula R$_3$(OCH$_2$CH$_2$)$_n$—, an aminoethylene moiety of the formula R$_3$(NHCH$_2$CH$_2$)$_n$—, or a thioether moiety of the formula R$_3$S(CH$_2$)$_n$—, wherein R$_3$ is H or linear C1–C12 alkyl and n is an integer from 1 to 15. Nonlimiting examples of suitable R groups include butyl, hexyl, octyl, 2-ethylhexyl, decyl, dodecyl, tetradecyl, hexadecyl, octadecyl, phenyl, cresyl (any isomer, attached at any ring position or at the phenolic oxygen), and mixtures thereof. Typically, the R groups will be one or more of butyl, 2-ethylhexyl, octyl, decyl, dodecyl, tetradecyl. R$_1$ and R$_2$ are each independently H or a C1–C4 alkyl group. Exemplary compositions according to the present invention are: 1,1'-thiobis(3-butoxypropan-2-ol), 1,1'-thiobis(3-octyloxypropan-2-ol), 1,1'-thiobis(3-decyloxypropan-2-ol), 1,1'-thiobis(3-(2-ethylhexyloxy)propan-2-ol), 1,1'-thiobis(3-dodecyloxypropan-2-ol), and 1,1'-thiobis(3-tetradecyloxypropan-2-ol).

Preparation of Compounds of Formula (I)

Compounds according to formula (I) may be prepared by any method known in the synthetic organic chemical art. In one exemplary embodiment of the invention, they may be prepared by the reaction of a sulfide source with a glycidyl ether according to formula (II), wherein R, $R_1$, and $R_2$ are as defined above, and wherein Z=S. Compounds wherein Z is SO or $SO_2$ may be made by oxidation of the corresponding compound where Z is S, using oxidation techniques well known in the art. In one exemplary embodiment of the invention oxidation is performed with hydrogen peroxide, but other methods may be used.

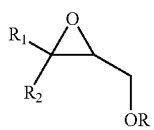
(II)

As used herein, the term "sulfide source" means a composition that contains, or otherwise provides, any of hydrogen sulfide, a bisulfide anion, or a sulfide anion. Suitable nonlimiting examples of sulfide sources include compounds $M_2S$ wherein each M is independently selected from the group consisting of H, $NH_4$, alkali metals, and alkaline earth metals. Specific examples of suitable sulfides and bisulfides include sodium sulfide, sodium bisulfide, potassium sulfide, potassium bisulfide, lithium sulfide, and lithium bisulfide in the anhydrous form or as hydrates. Other sulfide sources include alkali metal polysulfides and disulfides. The amount of glycidyl ether used in the reaction is typically from about 2.0 to about 5 moles per mole of sulfide, more typically from about 2 to about 3 moles, still more typically from about 2 to about 2.5 moles, and most typically about 2 moles per mole of sulfide. Mixtures of glycidyl ethers may be employed such that the reaction mixture will contain glycidyl ethers having two or more different R groups, two or more different $R_1$ groups, and/or two or more different $R_2$ groups. In such a situation, the product may include a mixture of compounds according to formula (I) in which some have the same R, $R_1$, and $R_2$ groups on both sides of the molecule, while others have different embodiments of any or all of these groups on one side vs. the other.

To prepare compounds according to formula (I), the sulfides or bisulfides may be reacted (adducted) with the glycidyl ether, which may optionally be dispersed in a reaction medium including a diluent, at a temperature sufficiently high so as to provide a convenient reaction rate and sufficiently low so as to prevent significant by-product formation. By "dispersed," it is meant that the glycidyl ether is suspended in the medium, dissolved in it, or a combination of these. The reaction temperature may be in the range from about 50° C. to about 150° C., preferably from about 50° C. to about 130° C., and more preferably from about 60° C. to about 90° C. The optimum conditions will depend upon the specific reactants, the reactor configuration, the solvents employed, and other variables. A variety of diluents may be used for the reaction, including liquids in which one or more of the reactants is essentially insoluble. More typically, a diluent (if used) will be a material that is a solvent for one or more of the reactants. Examples of suitable solvents include, but are not limited to, isopropanol, ethanol, methanol, acetonitrile, ethylene glycol, propylene glycol, combinations of water and acetonitrile, combinations of water and methanol, combinations of water and isopropanol, combinations of water and ethanol, and mixtures thereof. Typically, isopropanol will be used.

Uses of Compounds of Formula (I)

Compositions according to the invention may also include a variety of other ingredients adapted to complement the utility of compounds of formula (I) in a number of applications. The performance properties of such products may be optimized for a specific application by appropriate modification of the structure of the sulfide and the choice of the substituents R, $R_1$, and $R_2$. Such optimization is routine, and within the ability of the person of ordinary skill in the art in the particular application area. Thus manipulation of these variables yields compounds which may be useful as emulsifiers or detergents, wetting agents, foaming agents, defoamers, rheology modifiers or associative thickeners, dispersants, and the like. As such, these compounds may be useful in applications such as coatings, inks, adhesives, agricultural formulations, fountain solutions, photoresist strippers and developers, shampoos, and detergents and other cleaning compositions. The compounds may also find use in oil-field applications such as enhanced oil recovery, fracturing and stimulation processes, and drilling and cementing operations, and may also be useful in various wet-processing textile operations, such as dyeing of fibers and fiber scouring and kier boiling. The general formulation principles governing each of these applications are well known in the respective arts, and a detailed description of the numerous application areas and methods for incorporating the compounds of this invention into such formulations is not necessary to their effective incorporation therein. However, as an indication of the wide scope of possible uses for compounds according to the invention, exemplary but nonlimiting formulations are set forth below for a number of application areas.

The terms "water-based", "waterborne", "aqueous", or "aqueous medium", or "aqueous carrier" as used herein refer to systems in which the solvent or liquid dispersing medium comprises at least 50 wt % water, preferably at least 90 wt %, and more preferably at least 95 wt % water. The dispersing medium may consist essentially of water, i.e. it may have no added solvents.

By using compounds of formula (I), it is possible to reduce surface tension in a waterborne composition or an industrial process. Thus the invention provides aqueous compositions comprising such compounds, wherein the surfactant provides good wetting properties when used in a surfactant effective amount. For example, the amount of surfactant that is effective to provide enhanced wetting properties of a water-based, organic compound containing composition may range from 0.00001 to 5 wt %, preferably from 0.0001 to 3 wt %, and most preferably from 0.001 to 3 wt %, based on total weight of the formulation. The most favorable amount will vary from one application to another, depending upon the amount and type of other species present in the formulation that are capable of affecting foam properties and wetting performance, for example latex polymers.

A typical water-based coating formulation that includes the surfactants of the invention may include the following components in an aqueous medium, typically at 30 to 80% solids:

| Typical Aqueous-Based Coating Formulation | |
| --- | --- |
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting/Flow and Leveling Agents, other than Compound of Formula (I) |
| 0.001 to 5 wt % | Compound(s) of Formula (I) |

A typical water-based ink composition that includes the surfactants of the invention may include the following components in an aqueous medium at a 20 to 60% solids content (i.e. not including the coalescing solvent):

| Typical Aqueous-Based Ink Composition | |
| --- | --- |
| 1–50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-borne/water-dispersible/water-soluble resins |
| 0 to 30 wt % | Coalescing Solvents |
| 0.01 to 10 wt % | Surfactant/Wetting Agents, other than Compound(s) of Formula (I)s |
| 0.01 to 10 wt % | Processing Aids/Defoamers/Solubilizing Agents |
| 0.001 to 5 wt % | Compound(s) of Formula (I) |

A typical water-based agricultural composition that includes the surfactants of the invention may include the following components in an aqueous medium at 0.01 to 80% of the following ingredients:

| Typical Aqueous-Based Agricultural Composition | |
| --- | --- |
| 0.1–50 wt % | Pesticide or Plant Growth Modifying Agent |
| 0.01 to 10 wt % | Surfactants, other than Compound(s) of Formula (I)s |
| 0 to 5 wt % | Dyes |
| 0 to 20 wt % | Thickeners/Stabilizers/Co-surfactants/Gel Inhibitors/Defoamers |
| 0 to 25 wt % | Antifreeze agent (e.g. ethylene glycol or propylene glycol) |
| 0.001 to 5 wt % | Compound(s) of Formula (I) |

A typical fountain solution composition for planographic printing that includes the surfactants of the invention may include the following components:

| Typical Fountain Solution for Planographic Printing | |
| --- | --- |
| 0.05 to 10 wt % | Film forming, water soluble macromolecule |
| 1 to 25 wt % | C2–C12 Alcohol, glycol, or polyol (water soluble, or soluble due to use of a co-solvent) |
| 0.01 to 20 wt % | Water soluble organic acid, inorganic acid, or a salt of these |
| 30 to 98.9 wt % | Water |
| 0.001 to 5 wt % | Compound(s) of Formula (I) |

A typical hard surface cleaner that includes the surfactants of the invention may include the following components:

| Typical Hard Surface Cleaner | |
| --- | --- |
| 0 to 25 wt %* | Anionic surfactant |
| 0 to 25 wt %* | Cationic surfactant |
| 0 to 25 wt %* | Nonionic surfactant (e.g. alcohol alkoxylates, etc.) |
| 0 to 20 wt % | Chelating agent (EDTA, citrate, tartrate, etc.) |
| 0 to 25 wt %* | Solvent (Glycol ether, lower alcohols, etc.) |
| 0.001 to 25 wt % | Compound(s) of Formula (I) |
| 0 to 2 wt % | Dye, fragrance, preservative, etc. |
| 0 to 40 wt %* | Alkali metal hydroxide |
| Balance to 100 wt % | Water, and optionally other ingredients |

*To total, in combination, between 0.1 and 99 wt %.

A typical water-based photoresist developer or electronic cleaning composition that includes the surfactants of the invention may include the following components:

| Typical Aqueous-Based Photoresist Developer Composition | |
| --- | --- |
| 0.1 to 3 wt % | Tetramethylammonium hydroxide |
| 0 to 4 wt % | Phenolic resin |
| 92.5 to 99.9 wt % | Water |
| 0.001 to 5 wt % | Compound(s) of Formula (I) |

A typical metalworking fluid that includes the surfactants of the invention may include the following components:

| Typical Synthetic Metalworking Fluid Formulation | |
| --- | --- |
| 2.5 to 10 wt % | Block copolymer or other emulsifying agent |
| 10 to 25 wt % | Alkanolamine |
| 2 to 10 wt % | Organic monoacid |
| 0 to 5 wt % | Organic diacid |
| 40 to 84.4 wt % | Water |
| 1 to 5 wt % | Biocide |
| 0.001 to 5 wt % | Compound(s) of Formula (I) |

Surfactants are also used in a wide variety of products in the areas of personal care and household and industrial cleaning. The surfactants of the present invention may be used in any of these formulations to provide one or more benefits, with the exact structure of the surfactant compound depending upon the specific performance features required for a particular application. Typical formulations used in these markets are described in Louis Ho Tan Tai's book, *Formulating Detergents and Personal Care Products: A Complete Guide to Product Development* (Champaign, Ill.: AOCS Press, 2000) as well as in other books, literature, product formularies, etc. familiar to those 10 skilled in the art. A few representative example formulations are described here as illustrations. For example, a rinse aid for use in household automatic dishwashing or in industrial and institutional warewashing may have the ingredients described below.

| Typical Rinse Aid Formulation | |
| --- | --- |
| Compound(s) of Formula (I) | 0.001 to 45 wt % |
| Nonionic surfactant other than a compound of Formula (I) (e.g. alkoxylated alcohol(s), alkoxylated block copolymers, etc.) | 0 to 45 wt % |

Typical Rinse Aid Formulation

| | |
|---|---|
| Hydrotrope (e.g. sodium xylenesulfonate, sodium toluenesulfonate, anionic surfactant(s), amphoteric surfactant(s), etc.) | 0 to 10 wt % |
| Isopropyl alcohol or ethyl alcohol | 0 to 10 wt % |
| Chelant (e.g. citric acid, etc.) | 5 to 20 wt % |
| Water, and optionally other ingredients | Balance to 100 wt % |

Typical Powdered Laundry Detergent Formulation

| Material | Amount by Weight in Conventional Formulation | Amount by Weight in Concentrated Formulation |
|---|---|---|
| Compound(s) of Formula (I) | 0.001 to 5 wt % | 0.001 to 15 wt % |
| Detergent surfactant(s) (e.g. anionic surfactants, alcohol alkoxylates, etc.) | 0.1 to 30 wt % | 0.1 to 50 wt % |
| Builder/co-builder (zeolites, sodium carbonate, phosphates, etc.) | 25 to 50 wt % | 25 to 60 wt % |
| Bleach and bleach activator (perborates, etc.) | 0 to 25 wt % | 0 to 25 wt % |
| Other Additives (fragrance, enzymes, hydrotropes, etc.) | 0 to 7 wt % | 1 to 10 wt % |
| Fillers (sodium sulfate, etc.) | 5 to 35 wt % | 0 to 12 wt % |

Typical Aqueous Liquid Laundry Detergent Formulation

| Material | Amount by Weight in Conventional Formulation | Amount by Weight in Concentrated Formulation |
|---|---|---|
| Compound(s) of Formula (I) | 0.001 to 25 wt % | 0.001 to 30 wt % |
| Detergent surfactant(s) (e.g. anionic surfactants, alcohol alkoxylates, etc.) | 0 to 35 wt % | 0 to 65 wt % |
| Builder/co-builder (citrate, tartrate, etc.) | 3 to 30 wt % | 0 to 36 wt % |
| Other Additives (fragrances, dyes, etc.) | 0.1 to 5 wt % | 1 to 5 wt % |
| Water and other solvents (e.g. lower alcohols) | 5 to 75 wt % | 1 to 56 wt % |

Typical Non-Aqueous Laundry Detergent Formulation

| Material | Amount by Weight |
|---|---|
| Compound(s) of Formula (I) | 0.001 to 30 wt % |
| Detergent surfactant(s) (e.g. anionic surfactants, alcohol alkoxylates, amine oxides, etc.) | 0.1 to 42 wt % |
| Builder/co-builder (zeolites, sodium carbonate, phosphates, citrate or tartrate salts, etc.) | 25 to 60 wt % |
| Bleach and bleach activator (perborates, etc.) | 0 to 20 wt % |
| Anti-redeposition aids (sodium carboxymethylcellulose, etc.) | 0.5 to 5 wt % |
| Other Additives (fragrance, enzymes, etc.) | 0 to 5 wt % |
| Polyalkylene glycol | 0 to 50 wt % |

Typical 2-Part Industrial and Institutional Laundry Formulation

| | Amount by Weight of Material in Each Pack |
|---|---|
| Pack A | |
| Compound(s) of Formula (I) | 0.001 to 20 wt % |
| Detergent surfactant(s) (e.g. anionic surfactants, alcohol alkoxylates, etc.) | 0 to 20 wt % |
| Antiredeposition aids (sodium carboxymethylcellulose, etc.) | 0.01 to 2 wt % |
| Water, and optionally other ingredients | Balance to 100 wt % |
| Pack B | |
| Sodium silicate | 5 to 10 wt % |
| Sodium metasilicate | 0 to 30 wt % |
| Tetrapotassium pyrophosphate | 0 to 10 wt % |
| potassium hydroxide | 0 to 35 wt % |
| potassium carbonate | 0 to 15 wt % |
| Water, and optionally other ingredients | Balance to 100 wt % |
| Mix Ratio Pack A:Pack B | 1:2 to 1:4 |

Typical Shampoo or Liquid Body Wash Formulation

| Material | Amount by Weight |
|---|---|
| Compound(s) of Formula (I) | 0.001 to 5 wt % |
| Anionic surfactant(s) (e.g. sodium or ammonium lauryl sulfate, sodium or ammonium lauryl sulfate, etc.) | 0.1 to 30 wt % |
| Amphoteric cosurfactant(s) (e.g. cocoamidopropyl betaine, etc.) | 0 to 20 wt % |
| Nonionic surfactant other than a compound of Formula (I) (e.g. alcohol alkoxylates, sorbitan esters, alkyl glucosides, etc.) | 0 to 20 wt % |
| Cationic polymers (e.g. polyquaternium, etc.) | 0 to 5 wt % |
| Other Additives (fragrance, dyes, oils, opacifiers, preservatives, chelants, hydrotropes, etc.) | 0 to 15 wt % |
| Polymeric thickeners (e.g. polyacrylate, etc.) | 0 to 2 wt % |
| Conditioning oils (e.g. sunflower oil, petrolatum, etc.) | 0 to 10 wt % |
| Citric acid | 0 to 2 wt % |
| Ammonium chloride or sodium chloride | 0 to 3 wt % |
| Humectants (e.g. propylene glycol, glycerin, etc.) | 0 to 15 wt % |
| Glycol distearate | 0 to 5 wt % |
| Cocoamide (i.e. cocoamide MEA, cocoamide MIPA, PEG-5 cocoamide, etc.) | 0 to 10 wt % |
| Dimethicone | 0 to 5 wt % |
| Behenyl alcohol | 0 to 5 wt % |
| Water, and optionally other ingredients | Balance to 100 wt % |

Typical Hair Conditioner Formulation

| Material | Amount by Weight |
|---|---|
| Compound(s) of Formula (I) | 0.001 to 10 wt % |
| Nonionic surfactant other than a compound of Formula (I), and/or fatty alcohol(s) (e.g. stearyl alcohol, etc.) | 0.1 to 10 wt % |
| Cationic surfactant(s) (e.g. cetrimonium chloride, etc.) | 0 to 10 wt % |
| Anionic surfactants (e.g. TEA-dodecylbenzenesulfonate, etc.) | 0 to 5 wt % |
| Silicones (e.g. dimethicone, dimethiconal, etc.) | 0 to 5 wt % |
| Cationic polymers (e.g. polyquaternium, etc.) | 0 to 10 wt % |
| Other Additives (fragrance, dyes, oils, opacifiers, preservatives, chelants, hydrotropes, etc.) | 0 to 10 wt % |

Typical Hair Conditioner Formulation

| Material | Amount by Weight |
|---|---|
| Thickening polymers (e.g. hydroxyethylcellulose, polyacrylates, etc.) | 0 to 5 wt % |
| Potassium, ammonium or sodium chloride | 0 to 5 wt % |
| Humectant (e.g. propylene glycol, etc.) | 0 to 5 wt % |
| Panthenol | 0 to 2 wt % |
| Water, and optionally other ingredients | Balance to 100 wt % |

Typical Aqueous Sunscreen Formulation

| Material | Amount by Weight |
|---|---|
| Compound(s) of Formula (I) | 0.001 to 30 wt % |
| Polyethylene glycol (e.g. PEG-8, etc.) | 0 to 30 wt % |
| Active sunscreen agents (e.g. octyl methoxycinnamate, azobenzone, homosalate, octyl salicylate, oxybenzone, octocrylene, butyl methoxydibenzoylmethane, octyl triazone, etc.) | 1 to 30 wt % |
| Esters and emollients (e.g. dimethicone, methylparaben, propylparaben, polysorbates, etc.) | 0 to 20 wt % |
| Thickening polymers (e.g. acrylates/C10–30 alkyl acrylate crosspolymer, PVP/hexadecene copolymer, etc.) | 0 to 20 wt % |
| Other Additives (fragrance, dyes, oils, opacifiers, preservatives, chelants, etc.) | 0 to 20 wt % |
| Solvent/hydrotropes (e.g. propylene glycol, benzyl acohol, dicapryl ether, etc.) | 0 to 20 wt % |
| Triethanolamine | 0 to 5 wt % |
| Water, and optionally other ingredients | Balance to 100 wt % |

Cement Admixture Formulations

Cement admixtures may be of any of several types, including superplasticizing, plasticizing, accelerating, set retarding, air entraining, water-resisting, corrosion inhibiting, and other types. Such admixtures are used to control the workability, settling and end properties (strength, impermeability, durability and frost/deicing salt resistance, etc.) of cementitious products like concretes, mortars, etc. The admixtures are usually provided as aqueous solutions and they can be added to the cementitious system at some point during its formulation. Surfactants of this invention may provide wetting, foam control, flow and leveling, water reduction, corrosion inhibition, high ionic strength tolerance and compatibility, and other benefits when used in such systems.

Exemplary Cement Admixture Ingredients

| Material | Amount by Weight Relative to Cement Weight |
|---|---|
| Compound(s) of Formula (I) | 0.001 to 5 wt % |
| Solubilizing agents (solvent, hydrotropes, amines, etc.)* | 0 to 10 wt % |
| Polymers and/or oligomers (e.g. lignosulfonates, sulfonated melamine formaldehyde condensates, polycarboxylates, styrene-maleic anhydride oligomers, copolymers and their derivatives, etc.)* | 0 to 5 wt % |
| Functional Additives (defoamers, air entraining or detraining agents, pH control additives, corrosion inhibitors, set retarders, accelerators, preservatives, etc.)* | 0 to 5 wt % |
| Water | 40 to 75% |

*To total, in combination, between 0.1 and 20 wt %.

The present invention is further illustrated by the following examples, which are presented for purposes of demonstrating, but not limiting, the methods and compositions of this invention.

EXAMPLES

Example 1

Reaction of sodium bisulfide with butyl glycidyl ether

A solution of butyl glycidyl ether (2.91 g, 22.39 mmol) in isopropanol (5 mL) and $H_2O$ (1 mL) was added to sodium bisulfide (0.628 g, 11.20 mmol) under nitrogen in a 100 mL 3-neck round bottom flask equipped with a $N_2$ inlet, a rubber septum, glass stopper and a magnetic stir bar. The mixture was heated at 90° C. and monitored for completion by gas chromatography/mass spectrometry for disappearance of starting materials and formation of the product. After 3 h, the reaction was judged to be complete. The mixture was cooled to ambient temperature and treated with saturated $NH_4Cl$ (5.0 mL) and extracted into ethyl acetate (50 mL). The solvent was dried ($MgSO_4$), filtered, and evaporated in-vacuo to give the product, 1,1'-thiobis(3-butoxypropan-2-ol), which was identified by mass spectrometry as well as $^1H$ and $^{13}C$ NMR.

Example 1a

Reaction of sodium sulfide with butyl glycidyl ether

A reaction was carried out in a manner similar to that described in Example 1, starting from butyl glycidyl ether (2.91 g, 22.39 mmol) and sodium sulfide heptahydrate (2.69 g, 11.2 mmol). The product obtained was 1,1,-thiobis(3-butoxypropan-2-ol), identified as in Example 1.

Example 2

Reaction of sodium sulfide with Mixture of C12, C14, and C16 glycidyl ethers

A reaction was carried out in a manner similar to that described in Example 1, starting from sodium sulfide (22.48 g, 288 mmol) and a mixture of C12, C14, and C16 glycidyl ethers (139.62 g, ~576 mmol) in 100 mL of isopropanol and 47 mL of $H_2O$. The product, identified as in Example 1, was a mixture of 1,1,-thiobis(3-dodecyloxypropan-2-ol), 1,1,-thiobis(3-tetradecyloxypropan-2-ol), 1,1,-thiobis(3-hexadecyloxypropan-2-ol), and three analogous mixed species having, respectively, one dodecyloxy and one tetradecyloxy group, one hexadecyloxy and one tetradecyloxy group, and one hexadecyloxy and one dodecyloxy group.

Example 3

Reaction of sodium sulfide with a Mixture of C8 and C10 glycidyl ethers

A reaction was carried out in a manner similar to that described in Example 1, starting from sodium sulfide (22.48 g, 288 mmol) and a mixture of C8 and C10 glycidyl ethers (107.14 g ~576 mmol), in 100 mL of isopropanol and 47 mL of $H_2O$. The product, identified as in Example 1, was a mixture of 1,1,-thiobis(3-octyloxypropan-2-ol), 1,1,-thiobis (3-decyloxypropan-2-ol), and the analogous mixed species having one octyloxy and one decyloxy group.

Example 4

Reaction of sodium sulfide with 2-ethylhexyl glycidyl ether

A reaction was carried out in a manner similar to that described in Example 1, starting from sodium sulfide (22.48 g, 288 mmol) and 2-ethylhexyl glycidyl ether (576 mmol, 107.31 g) in 100 mL of isopropanol and 47 mL of $H_2O$. The product obtained was 1,1,-thiobis(3-(2-ethylhexyl)oxypropan-2-ol), identified as in Example 1.

The reactants and products of Examples 1–4 are shown in Table 1 below.

Examples 5–8

Equilibrium surface tensions

Equilibrium surface tensions were determined for the compounds prepared in Examples 1–4, using a Kruss K-12 tensiometer with a platinum Wilhelmy plate, maintaining the temperature at 25±1° C. by means of a constant temperature circulating bath. The results, reported in Table 2, are averages of 10 measurements over a 10-minute period, and have a standard deviation of less than 0.01 dyne/cm.

TABLE 2

Equilibrium Surface Tension Data for Sulfide/Glycidyl Ether Adducts

| Example | Compound | Surface Tension Dynes/cm (0.1 wt %) | Solubility |
|---|---|---|---|
| 5 | SBGE | 38.4 | <0.1 wt % |
| 6 | SOGE | 34.0 | <0.1 wt % |
| 7 | SEHGE | 37.9 | <0.1 wt % |
| 8 | SDDGE | 34.2 | <0.1 wt % |

TABLE 1

Sulfide/Glycidyl Ether Adducts

| Example | sulfide | Glycidyl Ether | Product |
|---|---|---|---|
| 1 | $Na_2S$ | butyl glycidyl ether | $C_4H_9O$-CH$_2$-CH(OH)-CH$_2$-S-CH$_2$-CH(OH)-CH$_2$-O-$C_4H_9$ (SBGE) |
| 2 | $Na_2S$ | glycidyl ether, R = mix of $C_{12}H_{25}$, $C_{14}H_{29}$, $C_{16}H_{33}$ | RO-CH$_2$-CH(OH)-CH$_2$-S-CH$_2$-CH(OH)-CH$_2$-O-R, R = mix of $C_{12}H_{25}$, $C_{14}H_{29}$, $C_{16}H_{33}$ (SDDGE) |
| 3 | $Na_2S$ | glycidyl ether, R = mix of $C_8H_{17}$, $C_{10}H_{21}$ | RO-CH$_2$-CH(OH)-CH$_2$-S-CH$_2$-CH(OH)-CH$_2$-O-R, R = mix of $C_8H_{17}$, $C_{10}H_{21}$ (SOGE) |
| 4 | $Na_2S$ | 2-ethylhexyl glycidyl ether | 1,1,-thiobis(3-(2-ethylhexyl)oxypropan-2-ol) (SEHGE) |

Examples 9–12

Foam Characteristics of sulfide/glycidyl ether adducts

Foam height and stability (time to reach zero foam) were measured by the Ross-Miles foam test, using 0.1 wt % solutions of the surfactants. The results of these determinations are presented in Table 3.

TABLE 3

Foam Stability Data

| Example | Compound | Initial Foam Height (cm) | Time to 0 foam (sec) |
|---|---|---|---|
| 9 | SBGE | 0.7 | 2 |
| 10 | SOGE | 0 | 0 |
| 11 | SEHGE | 0 | 0 |
| 12 | SDDGE | 0 | 0 |

The data in Table 3 demonstrate that a range of foam performance may be obtained, depending upon the glycidyl ether capping group. While applications such as coatings, inks, and adhesives require low foam or foam that dissipates quickly, other applications such as cleaning or ore floatation require a controlled amount of foam to be present arid to persist. Therefore, compositions incorporating compounds according to formula (I) may find utility in a wide range of applications.

Examples 13–16

Dynamic surface tension data

Dynamic surface tensions were determined for the compounds prepared in Examples 1–4, at 0.1 and 1.0 wt % levels, using a Kruss BP-2 Bubble Pressure Tensiometer. The results of these determinations are shown in Table 4.

TABLE 4

Dynamic Surface Tension

| | | Dynamic surface tension (dynes/cm), 0.1 wt % | | | Dynamic surface tension (dynes/cm), 1.0 wt % | | |
|---|---|---|---|---|---|---|---|
| Example | Compound | 1 b/s | 5 b/s | 20 b/s | 1 b/s | 5 b/s | 20 b/s |
| 13 | SBGE | 37 | 38 | 38 | 36 | 37 | 38 |
| 14 | SOGE | 70 | 71 | 71 | 68 | 70 | 71 |
| 15 | SEHGE | 61 | 68 | 69 | 52 | 57 | 59 |
| 16 | SDDGE | 72 | 72 | 70 | 36 | 50 | 52 | b/s = bubbles/second

The data in Table 4 show that a wide range of dynamic surface tension reduction is possible with this family of molecules providing differing surfactants for strong (Example 13) or moderate (Example 16), surface tension reduction of an aqueous solution or formulation. Depending upon the mode of application of a formulation and the substrate to be wetted (brush application of an industrial coating, spray application of an industrial cleaner, roller application of an adhesive), surfactants that provide such a wide range of dynamic surface tension reduction may find significant commercial utility.

Example 17

Preparation of 1,1'-bis(3-octyloxypropan-2-ol) sulfoxide and 1,1'-bis(3-octyloxypropan-2-ol) sulfone A solution of 1,1-thiobis(3-octyloxypropan-2-ol) (5.0 g, 12.32 mmol) in isopropanol (20 mL) was treated with a 30% solution of $H_2O_2$ in water (11.2 mL, 98.52 mmol) under nitrogen in a 100 mL 3-neck round bottom flask equipped with an $N_2$ inlet, a rubber septum, a glass stopper and a magnetic stir bar. The mixture was heated at 60° C. for 24 h. The mixture was cooled to ambient temperature and treated with an aqueous saturated $NaHSO_3$ solution (5.0 mL) and extracted into ethyl acetate (50 mL). The solvent was dried ($MgSO_4$), filtered, and evaporated in-vacuo to give the product as a 1:1 mixture of 1,1'-bis(3-octyloxypropan-2-ol) sulfoxide and 1,1'-bis(3-octyloxypropan-2-ol) sulfone, which were identified by mass spectrometry as well as $^1H$ and $^{13}C$ NMR.

This invention provides novel surfactants with properties that make suitable for use in a wide range of industrial and commercial applications. Such applications include water-based coatings, inks, adhesives, agricultural formulations, aqueous and non-aqueous cleaning compositions, personal care applications, and formulations for textile processing and oilfield applications.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

What is claimed:

1. A composition comprising a compound according to formula (I)

$$ROCH_2CH(OH)CR_1R_2ZCR_1R_2CH(OH)CH_2OR \quad (I)$$

wherein each R is independently selected from the group consisting of C4–C20 branched, linear, and cyclic alkyl, and aryl moieties; C4–C20 branched, linear, and cyclic alkyl, alkenyl, aryl, and aralkyl moieties bearing a carbonyl group or one or more heteroatoms selected from O, S, and N; glycol ether moieties of the formula $R_3(OCH_2CH_2)_n$—; aminoethylene moieties of the formula $R_3(NHCH_2CH_2)_n$—; and thioether moieties of the formula $R_3S(CH_2)_n$—; wherein $R_3$ is H or linear C1–C12 alkyl and n is an integer from 1 to 15, $R_1$ and $R_2$ are each independently H or a C1–C4 alkyl group, and Z is S, SO, or $SO_2$.

2. The composition of claim 1, wherein Z is S.

3. A composition comprising a compound according to formula (I)

$$ROCH_2CH(OH)CR_1R_2ZCR_1R_2CH(OH)CH_2OR \quad (I)$$

wherein each R is independently selected from the group consisting of C4–C20 branched, linear, and cyclic alkyl, alkenyl, aryl, and aralkyl moieties; C4–C20 branched, linear, and cyclic alkyl, alkenyl, aryl, and aralkyl moieties bearing a carbonyl group or one or more heteroatoms selected from O, S, and N; glycol ether moieties of the formula $R_3(OCH_2CH_2)_n$—; aminoethylene moieties of the formula $R_3(NHCH_2CH_2)_n$—; and thioether moieties of the formula $R_3S(CH_2)_n$—; wherein $R_3$ is H or linear C1–C12 alkyl and n is an integer from 1 to 15, $R_1$ and $R_2$ are each independently H or a C1–C4 alkyl group, and Z is SO or $SO_2$.

4. The composition of claim 1, wherein $R_1$ and $R_2$ are each H.

5. The composition of claim 1, wherein each R is independently selected from the group consisting of C4–C20 linear alkyl moieties.

6. The composition of claim 1, wherein the compound according to formula (I) is 1,1'-thiobis(3-butoxypropan-2-ol).

7. The composition of claim 1, wherein the compound according to formula (I) is 1,1'-thiobis(3-(2-ethylhexyloxy)propan-2-ol).

8. The composition of claim 1, wherein the compound according to formula (I) is 1,1'-thiobis(3-octyloxypropan-2-ol).

9. The composition of claim 1, wherein the compound according to formula (I) is 1,1'-thiobis(3-decyloxypropan-2-ol).

10. The composition of claim 1, wherein the compound according to formula (I) is 1,1'-thiobis(3-dodecyloxypropan-2-ol).

11. The composition of claim 1, wherein the compound according to formula (I) is 1,1'-thiobis(3-tetradecyloxypropan-2-ol).

12. The composition of claim 1, further comprising a surfactant selected from the group consisting of anionic surfactants, cationic surfactants, amphoteric surfactants, and nonionic surfactants.

13. The composition of claim 1, further comprising a film-forming resin and an aqueous carrier.

14. The composition of claim 1, further comprising an aqueous carrier and a pesticide or plant growth modifying agent.

15. The composition of claim 1, further comprising a water-soluble film-forming resin, a C2–C12 alcohol, glycol, or polyol, an organic or inorganic acid or salt thereof, and an aqueous carrier.

16. The composition of claim 1, further comprising a glycol ether, a buffering agent, and an aqueous carrier.

17. The composition, of claim 1, further comprising tetramethylammonium hydroxide and an aqueous carrier.

18. The composition of claim 1, further comprising an emulsifier, an alkanolamine, an organic monoacid, and an aqueous carrier.

19. The composition of claim 1, further comprising a laundry detergent builder.

20. The composition of claim 1, further comprising a sunscreen agent.

21. In a hard surface cleaning formulation comprising water and between 0.1 and 99 wt % in total of one or more ingredients selected from the group consisting of anionic surfactants, cationic surfactants, nonionic surfactants other than according to formula (I) of claim 1, solvents, and alkali metal hydroxides, the improvement comprising including in the formulation between 0.001 and 25 wt % of the composition of claim 1.

22. In a coating formulation comprising between 5 and 99.9 wt % of a water-borne, water-dispersible, or water-soluble resin, and between 0.01 and 10 wt % in total of one or more other additives selected from the group consisting of surfactants, wetting agents, and flow and leveling agents, other than according to formula (I) of claim 1, the improvement comprising including in the formulation between 0.001 and 5 wt % of the composition of claim 1.

23. In an ink formulation comprising between 1 and 50 wt % of a pigment, between 5 and 99.9 wt % of a water-borne, water-dispersible, or water-soluble resin, between 0.01 and 10 wt % of a surfactant or wetting agent other than according to formula (I) of claim 1, and between 0.01 and 10 wt % in total of one or more other additives selected from the group consisting of processing aids, defoamers, and solubilizing agents, the improvement comprising including in the formulation between 0.001 and 5 wt % of the composition of claim 1.

24. In an agricultural formulation comprising between 0.1 and 50 wt % of a pesticide or plant growth modifying agent and between 0.01 and 10 wt % of a surfactant or wetting agent other than according to formula (I) of claim 1, the improvement comprising including in the formulation between 0.001 and 5 wt % of the composition of claim 1.

25. In a fountain solution formulation for planographic printing comprising between 0.05 and 10 wt % of a water-soluble, film forming macromolecule, between 1 and 25 wt % of a water-soluble alcohol, glycol, or polyol, between 0.01 and 20 wt % of a water-soluble acid or its salt, and between 30 and 98.9 wt % of water, the improvement comprising including in the formulation between 0.001 and 5 wt % of the composition of claim 1.

26. In a photoresist developer formulation comprising between 0.1 and 3 wt % of tetramethylammonium hydroxide and between 92.5 and 99.9 wt % of water, the improvement comprising including in the formulation between 0.001 and 5 wt % of the composition of claim 1.

27. In a synthetic metalworking fluid formulation comprising between 2.5 and 10 wt % of an emulsifying agent, between 10 and 25 wt % of an alkanolamine, between 2 and 10 wt % of an organic monoacid, between 1 and 5 wt % of a biocide, and between 40 and 84.4 wt % of water, the improvement comprising including in the formulation between 0.001 and 5 wt % of the composition of claim 1.

28. In a rinse aid formulation comprising water and between 5 and 20 wt % of a chelant, the improvement comprising including in the formulation between 0.001 and 45 wt % of the composition of claim 1.

29. In a powdered laundry detergent formulation comprising between 0.1 and 50 wt % of one or more detergent surfactants and between 25 and 60 wt % of a builder or co-builder, the improvement comprising including in the formulation between 0.001 and 15 wt % of the composition of claim 1.

30. In an aqueous liquid laundry detergent formulation comprising between 0.1 and 65 wt% of one or more detergent surfactants, between 3 and 36 wt % of a builder or co-builder, between 0.1 and 5 wt % in total of one or more other additives selected from the group consisting of fragrances and dyes, and between 1 and 75 wt % in total of one or more other additives selected from the group consisting of water and other solvents, the improvement comprising including in the formulation between 0.001 and 30 wt % of the composition of claim 1.

31. In a non-aqueous laundry detergent formulation comprising between 0.1 and 42 wt % of one or more detergent surfactants, between 25 and 60 wt % of a builder or co-builder, and between 0.5 and 5 wt % of an anti-redeposition aid, the improvement comprising including in the formulation between 0.001 and 30 wt % of the composition of claim 1.

32. In an industrial and institutional laundry detergent formulation comprising water and between 0.01 and 2 wt % of an anti-redeposition aid, the improvement comprising including in the formulation between 0.001 and 20 wt % of the composition of claim 1.

33. In a shampoo or liquid body wash formulation comprising water and between 0.1 and 30 wt % of an anionic surfactant, the improvement comprising including in the formulation between 0.001 and 5 wt % of the composition of claim 1.

34. In a hair conditioner formulation comprising water and between 0.1 and 10 wt % of a nonionic surfactant other than according to formula (I) of claim 1, the improvement comprising including in the formulation between 0.001 and 10 wt % of the composition of claim 1.

35. In an aqueous sunscreen formulation comprising water and between 1 and 30 wt % of a sunscreen agent, the improvement comprising including in the formulation between 0.001 and 30 wt % of the composition of claim 1.

36. In a cement admixture formulation comprising between 40 and 75 wt % of water and between 0.1 and 20 wt % in total of one or more solubilizing agents, polymers, oligomers, or functional additives, the improvement comprising including in the formulation between 0.001 and 5 wt % of the composition of claim 1.

37. The composition of claim 5, wherein $R_1$ and $R_2$ are both H and Z is S.

* * * * *

UNITED STATES PATENT AND TRADEMARK OFFICE
CERTIFICATE OF CORRECTION

| | |
|---|---|
| PATENT NO. | : 7,049,472 B2 |
| APPLICATION NO. | : 10/899419 |
| DATED | : May 23, 2006 |
| INVENTOR(S) | : Gauri Sankar Lal et al. |

Page 1 of 1

It is certified that error appears in the above-identified patent and that said Letters Patent is hereby corrected as shown below:

Column 14, lines 42 & 43
    Delete "and aryl" and substitute therefor -- alkenyl, and aryl, and aralkyl moieties; --

Signed and Sealed this

Twelfth Day of February, 2008

JON W. DUDAS
*Director of the United States Patent and Trademark Office*